(12) United States Patent
Nirogi et al.

(10) Patent No.: US 9,328,092 B2
(45) Date of Patent: May 3, 2016

(54) ACRYLAMIDE COMPOUNDS AS HISTAMINE H3 RECEPTOR LIGANDS

(71) Applicant: Suven Life Sciences Limited, Hyderabad (IN)

(72) Inventors: Ramakrishna Nirogi, Hyderbad (IN); Anil Karbhari Shinde, Hyderabad (IN); Adi Reddy Dwarampudi, Hyderabad (IN); Venkateswarlu Jasti, Hyderabad (IN)

(73) Assignee: Suven Life Sciences Limited (IN)

( * ) Notice: Subject to any disclaimer, the term of this patent is extended or adjusted under 35 U.S.C. 154(b) by 0 days.

(21) Appl. No.: 14/419,474

(22) PCT Filed: Dec. 5, 2012

(86) PCT No.: PCT/IN2012/000796
§ 371 (c)(1),
(2) Date: Feb. 3, 2015

(87) PCT Pub. No.: WO2014/030170
PCT Pub. Date: Feb. 27, 2014

(65) Prior Publication Data
US 2015/0218129 A1    Aug. 6, 2015

(30) Foreign Application Priority Data

Aug. 23, 2012   (IN) .......................... 3464/CHE/2012

(51) Int. Cl.
*C07D 401/12*   (2006.01)
*C07D 211/46*   (2006.01)
*C07C 55/02*    (2006.01)

(52) U.S. Cl.
CPC .............. *C07D 401/12* (2013.01); *C07C 55/02* (2013.01); *C07D 211/46* (2013.01)

(58) Field of Classification Search
CPC ........................... C07D 401/12; C07D 211/46
USPC ................................ 514/235.5; 544/124, 129
See application file for complete search history.

(56) References Cited

FOREIGN PATENT DOCUMENTS

| WO | WO-2005117865 A1 | 12/2005 |
| WO | WO-2005123716 A1 | 12/2005 |
| WO | WO-2009013195 A1 | 1/2009 |

OTHER PUBLICATIONS

International Application No. PCT/IN2012/000796, International Search Report mailed May 24, 2013, 3 pgs.
International Application No. PCT/IN2012/000796, International Preliminary Report on Patentability mailed Jul. 28, 2014, 5 pgs.

*Primary Examiner* — Kahsay Habte
(74) *Attorney, Agent, or Firm* — Schwegman, Lundberg & Woessner, P.A.

(57) ABSTRACT

The present invention relates to novel acrylamide compounds of formula (I):

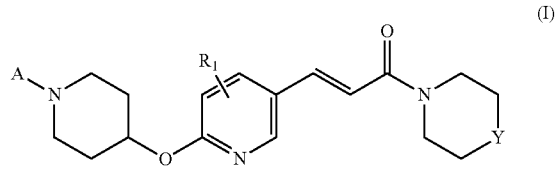

wherein A, X, $R^1$, and Y are as defined herein, and their pharmaceutically acceptable salts and process of their preparation. The compounds of formula (I) are useful in the treatment of various disorders that related to Histamine $H_3$ receptors.

6 Claims, No Drawings

ACRYLAMIDE COMPOUNDS AS HISTAMINE H3 RECEPTOR LIGANDS

This application is a U.S. National Stage Filing under 35 U.S.C. 371 from International Application No. PCT/IN2012/000796, entitled "ACRYLAMIDE COMPOUNDS AS HISTAMINE H3 RECEPTOR LIGANDS," filed on Dec. 5, 2012, and published as WO 2014/030170 A1 on Feb. 27, 2014, which claims the benefit of priority under 35 U.S.C. §119 to Indian Provisional Patent Application No. 3464/CHE/2012, filed on Aug. 23, 2012, which are hereby incorporated by reference herein in their entireties.

FIELD OF THE INVENTION

The present invention relates to novel acrylamide compounds of formula (I) and their pharmaceutically acceptable salts, for treatment of various disorders that are related to Histamine $H_3$ receptors.

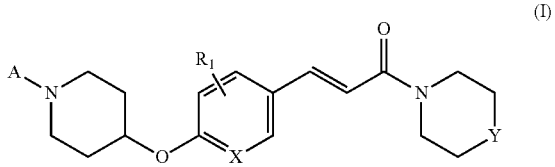

BACKGROUND OF THE INVENTION

Histamine $H_3$ receptor is a G-protein coupled receptor (GPCR) and one out of the four receptors of Histamine family. Histamine $H_3$ receptor is identified in 1983 and its cloning and characterization were done in 1999. Histamine $H_3$ receptor is expressed to a larger extent in central nervous system and lesser extent in the peripheral nervous system.

Literature evidence suggests that Histamine $H_3$ receptor ligands can be used in treatment of cognitive disorders (British Journal of Pharmacology, 2008, 154(6), 1166-1181), dementia (Drug News Perspective, 2010, 23(2), 99-103), attention deficit hyperactivity disorder, obesity (Indian Journal of Pharmacology, 2001, 33, 17-28), schizophrenia (Biochemical Pharmacology, 2007, 73(8), 1215-1224) and pain (Journal of Pharmacology and Experimental Therapeutics, 2011, 336(1), 30-37).

Patent publications WO 2007/137955, US 2009/0170869, US 2010/0029608, US 2010/0048580, WO 2009/100120, WO 2009/121812 and WO 2009/135842 disclosed series of compounds as ligands at Histamine $H_3$ receptors. While some Histamine $H_3$ receptor ligands have been disclosed, no compound till date is launched in market in this area of research, and there still exists a need and scope to discover new drugs with novel chemical structures for treatment of disorders affected by Histamine $H_3$ receptors.

SUMMARY OF THE INVENTION

The present invention relates to novel acrylamide Histamine $H_3$ receptor ligands of the formula (I),

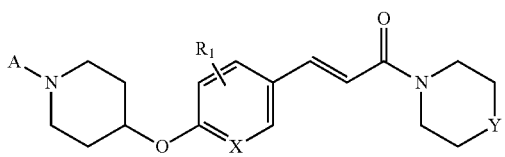

wherein,
at each occurrence, $R_1$ is independently selected from hydrogen, halogen, alkyl or alkoxy;
"A" is alkyl, cycloalkyl or cycloalkylalkyl;
"X" is C or N;
"Y" is C, O or

or its pharmaceutically acceptable salts.

The present invention relates to use of a therapeutically effective amount of compound of formula (I), to manufacture a medicament in the treatment of various disorders that are related to Histamine $H_3$ receptors.

Specifically, the compounds of this invention are useful in the treatment of various disorders such as cognitive deficits in schizophrenia, narcolepsy, obesity, attention deficit hyperactivity disorder, pain or alzheimer's disease.

In another aspect, the invention relates to pharmaceutical compositions containing a therapeutically effective amount of at least one compound of formula (I), or its their pharmaceutically acceptable salts thereof, in admixture with pharmaceutically acceptable excipient.

In still another aspect, the invention further relates to the process for preparing compounds of formula (I) and their pharmaceutically acceptable salts.

Representative compounds of the present invention include those specified below and their pharmaceutically acceptable salts. The present invention should not be construed to be limited to them.

3-[4-(1-Cyclobutyl piperidin-4-yloxy)phenyl]-1-(morpholin-4-yl)prop-2-ene-1-one fumarate salt;
3-[4-(1-Cyclobutyl piperidin-4-yloxy)phenyl]-1-(piperidin-1-yl)prop-2-ene-1-one hydrochloride salt;
3-[4-(1-Cyclobutyl piperidin-4-yloxy)phenyl]-1-(1,1-dioxo thiomorpholin-4-yl)prop-2-ene-1-one hydrochloride salt;
3-[2-(1-Cyclobutyl piperidin-4-yloxy)pyridin-5-yl]-1-(piperidin-1-yl)prop-2-ene-1-one L(+)-Tartarate salt;
3-[2-(1-Cyclobutyl piperidin-4-yloxy)pyridin-5-yl]-1-(morpholin-4-yl)prop-2-ene-1-one L(+)-Tartarate salt;
3-[2-Fluoro-4-(1-isopropyl piperidin-4-yloxy)phenyl]-1-(morpholin-4-yl)prop-2-ene-1-one L(+)-Tartarate salt;
3-[2-Fluoro-4-(1-cyclobutyl piperidin-4-yloxy)phenyl]-1-(morpholin-4-yl)prop-2-ene-1-one L(+)-Tartarate salt;
3-[4-(1-Cyclobutyl piperidin-4-yloxy)-2-methyl phenyl]-1-(morpholin-4-yl)prop-2-ene-1-one L(+)-Tartarate salt;
3-[4-(1-Isopropyl piperidin-4-yloxy)-2-methyl phenyl]-1-(morpholin-4-yl)prop-2-ene-1-one L(+)-Tartarate salt;
3-[4-(1-Cyclobutyl piperidin-4-yloxy)phenyl]-1-(morpholin-4-yl)prop-2-ene-1-one L(+)-Tartarate salt;
3-[4-(1-Cyclobutyl piperidin-4-yloxy)-3-methoxy phenyl]-1-(morpholin-4-yl)prop-2-ene-1-one L(+)-Tartarate salt;
3-[4-(1-Cyclopropylmethyl piperidin-4-yloxy)-3-methoxy phenyl]-1-(morpholin-4-yl)prop-2-ene-1-one L(+)-Tartarate salt;
3-[4-(1-Isobutyl piperidin-4-yloxy)-3-methoxy phenyl]-1-(morpholin-4-yl)prop-2-ene-1-one L(+)-Tartarate salt;
3-[4-(1-Isopropyl piperidin-4-yloxy)-3-methoxy phenyl]-1-(morpholin-4-yl)prop-2-ene-1-one L(+)-Tartarate salt;

3-[4-(1-Isopropyl piperidin-4-yloxy)-3-methoxy phenyl]-1-(piperidin-1-yl)prop-2-ene-1-one L(+)-Tartarate salt;
3-[4-(1-Cyclobutyl piperidin-4-yloxy)-3-methoxy phenyl]-1-(piperidin-1-yl)prop-2-ene-1-one L(+)-Tartarate salt;
3-[4-(1-Cyclopropylmethyl piperidin-4-yloxy)phenyl]-1-(morpholin-4-yl)prop-2-ene-1-one;
3-[4-(1-Isobutyl piperidin-4-yloxy)phenyl]-1-(morpholin-4-yl)prop-2-ene-1-one;
3-[3-Bromo-4-(1-isopropyl piperidin-4-yloxy)phenyl]-1-(morpholin-4-yl)prop-2-ene-1-one;
3-[3-Bromo-4-(1-cyclobutyl piperidin-4-yloxy)phenyl]-1-(morpholin-4-yl)prop-2-ene-1-one;
3-[3-Bromo-4-(1-isobutyl piperidin-4-yloxy)phenyl]-1-(morpholin-4-yl)prop-2-ene-1-one;
3-[3-Bromo-4-(1-cyclopropylmethyl piperidin-4-yloxy)phenyl]-1-(morpholin-4-yl)prop-2-ene-1-one;
3-[6-(1-Cyclopropylmethyl piperidin-4-yloxy)pyridin-3-yl]-1-(morpholin-4-yl)prop-2-ene-1-one L(+)-Tartarate salt;
3-[6-(1-Isobutyl piperidin-4-yloxy)pyridin-3-yl]-1-(morpholin-4-yl)prop-2-ene-1-one L(+)-Tartarate salt;
3-[2-Chloro-4-(1-cyclobutyl piperidin-4-yloxy)phenyl]-1-(morpholin-4-yl)prop-2-ene-1-one;
3-[2-Chloro-4-(1-isopropyl piperidin-4-yloxy)phenyl]-1-(morpholin-4-yl)prop-2-ene-1-one;
3-[2-Chloro-4-(1-cyclopropylmethyl piperidin-4-yloxy)phenyl]-1-(morpholin-4-yl)prop-2-ene-1-one; or
3-[2-Chloro-4-(1-isobutyl piperidin-4-yloxy)phenyl]-1-(morpholin-4-yl)prop-2-ene-1-one.

DETAILED DESCRIPTION OF THE INVENTION

Unless otherwise stated, the following terms used in the specification and claims have the meanings given below:

The term "halogen" means fluorine, chlorine, bromine or iodine.

The term "alkyl" means straight chain or branched hydrocarbon radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "alkoxy" means an alkyl group attached via an oxygen linkage to the rest of the molecule. Exemplary "alkoxy" groups include methoxy, ethoxy, propyloxy, iso-propyloxy and the like.

The term "cycloalkyl" means non-aromatic mono cyclic ring of 3 to 8 carbon atoms.

Exemplary "cycloalkyl" groups include cyclopropyl, cyclobutyl, cyclopentyl and the like.

The term "cycloalkylalkyl" means non-aromatic mono cyclic ring of 3 to 8 carbon atoms attached to an alkyl group. Exemplary "cycloalkylalkyl" groups include cyclopropyl methyl, cyclobutyl methyl, cyclopentyl methyl and the like.

The phrase "pharmaceutically acceptable salts" indicates that the substance or composition must be compatible chemically and/or toxicologically, with the other ingredients comprising a formulation, the mammal being treated therewith.

The phrase "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

Commercial reagents were utilized without further purification. Room temperature refers to 25-40° C. Unless otherwise stated, all mass spectra were carried out using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million ($\delta$) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable excipient. The pharmaceutically acceptable excipient is carrier or diluent. Thus, the active compounds of the invention may be formulated for oral, intranasal or parenteral (e.g., intravenous, intramuscular or subcutaneous). Such pharmaceutical compositions and processes for preparing same are well known in the art (The Science and Practice of Pharmacy, D. B. Troy, 21st Edition, Williams & Wilkins, 2006).

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors Methods of Preparation The compounds of formula (I) can be prepared by Scheme I as shown below.

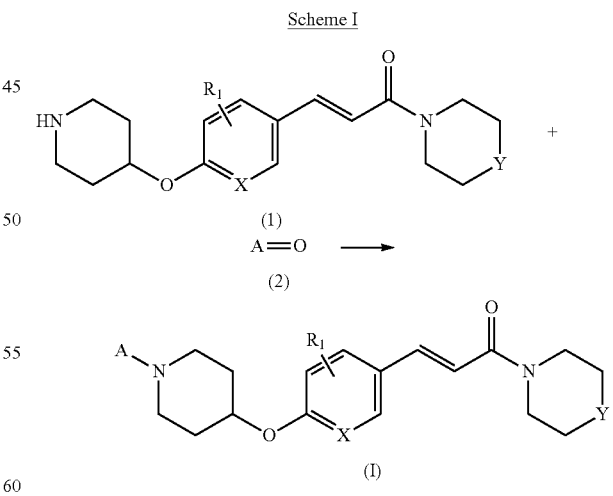

Reductive amination of the compound of formula (1) with compound of formula (2) to form compound of formula (I). This reaction is preferably carried out in solvent such as tetrahydrofuran, toluene, ethyl acetate, dichloromethane, dimethylformamide, and the like or a mixture thereof and preferably, by using dichloromethane. The reaction may be affected in the presence of a reducing agent such as diisobutylaluminum hydride, sodium triacetoxyborohydride, dimethylsulfide borane, sodium bis(2-methoxyethoxy)aluminumhydride, sodium hydrosulfite, sodium borohydride, sodium cyanoborohydride and sodium dithionite and preferably by using sodium triacetoxyborohydride. The reaction is carried out at room temperature. The duration of the reaction may range from 4 hours to 8 hours, preferably from a period of 5 hours to 7 hours.

Compounds of formula (1) can be prepared by using preparations 1 & 2 or can be prepared by using conventional methods or by modifications using known process.

Compounds of formula (2) may be commercially available or can be prepared by conventional methods or by modification using known process.

The pharmaceutically acceptable salts forming a part of this invention may be prepared by treating the compound of formula (I) with 1-6 equivalents of a acids such as hydrochloric, hydrobromic, sulfuric, nitric, phosphoric acid, succinic, maleic, acetic, fumaric, citric, malic, tartaric, benzoic, p-toluic, p-toluenesulfonic, methanesulfonic or naphthalenesulfonic acid. The most preferable salts of compounds of formula (I) are fumarate, L(+)-tartarate, hydrochloride, oxalate and sulfate.

EXAMPLES

The novel compounds of the present invention were prepared according to the following experimental procedures, using appropriate materials and appropriate conditions.

Preparation 1: Preparation of 3-[4-(Piperidin-4-yloxy)phenyl]-1-(morpholin-4-yl)prop-2-ene-1-one

Step (i): Preparation of t-Butyl 4-(4-formyl phenoxy)piperidine-1-carboxylate A solution of 4-Hydroxybenzaldehyde (20.1 grams, 0.164 moles), potassium carbonate (67.9 grams, 0.492 moles) and t-butyl 4-(toluene-4-sulfonyloxy)piperidine-1-carboxylate (70 grams, 0.197 moles) in acetonitrile (1000 mL) was stirred for 18 hours at 80° C. The progress of the reaction was monitored by thin layer chromatography. After completion of reaction, the mass was cooled to room temperature and quenched on to chilled water (1000 mL). The compound was extracted with dichloromethane (3×500 mL). The resulting dichloromethane layer was washed with 10% lye solution (100 mL), water (100 mL) and brine solution (100 mL). The organic phase was dried over sodium sulfate and concentrated under reduced pressure to afford the title compound (50.3 grams).

Yield: 100%.

$^1$H-NMR (δ ppm): 1.48 (9H, s), 1.76-1.83 (2H, m), 1.96-2.04 (2H, m), 3.36-3.41 (2H, m), 3.68-3.73 (2H, m), 4.45-4.60 (1H, m), 6.96-7.02 (2H, m), 7.78-7.85 (2H, m), 9.89 (1H, s);

Mass (m/z): 306.4 (M+H)$^+$.

Step (ii): Preparation of 3-[4-(1-t-Butyloxycarbonyl piperidin-4-yloxy)phenyl]prop-2-ene-1-oic acid A solution of t-Butyl 4-(4-formyl phenoxy)piperidine-1-carboxylate (50.2 grams, 0.164 moles, obtained in above step), malonic acid (50.6 grams, 0.486 moles) and piperidine (12.5 mL) in pyridine (250 mL) was stirred for 8 hours at 110° C. under nitrogen atmosphere.

The progress of the reaction was monitored by thin layer chromatography. After completion of reaction, the mass was concentrated and the resulting slurry was triturated with n-hexane (200 mL) and stirred for 30 minutes. The solids, thus obtained, were washed with n-hexane (100 mL) and dried under vacuum to afford the title compound (39.1 grams).

Yield: 68%.

$^1$H-NMR (δ ppm): 1.47 (9H, s), 1.76-1.80 (2H, m), 1.90-1.96 (2H, m), 3.35-3.40 (2H, m), 3.67-3.72 (2H, m), 4.53-4.60 (1H, m), 6.30-6.34 (1H, d, J=15.32 Hz), 6.89-6.95 (2H, d, J=8.64); 7.47-7.53 (2H, d, J=8.64 Hz), 7.71-7.75 (1H, d, J=15.33 Hz);

Mass (m/z): 348.2 (M+H)$^+$.

Step (iii): Preparation of 3-[4-(1-t-Butyloxycarbonyl piperidin-4-yloxy)phenyl]-1-(morpholin-4-yl)prop-2-ene-1-one To a stirred solution of 3-[4-(1-t-butyloxycarbonyl piperidin-4-yloxy)phenyl]prop-2-ene-1-oic acid (38 grams, 0.109 moles, obtained in above step) and triethylamine (38.4 mL, 0.273 moles) in dichloromethane (500 mL) was added ethylchloroformate (13.6 mL, 0.142 moles) at 0° C. The reaction mass was further stirred for 2 hours at 0-5° C. Morpholine (19.2 mL, 0.219 moles) was added to above mass at 0-5° C. and the resulting mixture were stirred for 2 hours. The progress of the reaction was monitored by thin layer chromatography. After completion of reaction, the mass was quenched by adding water (100 mL). Layers were separated and the organic layer was washed with brine solution (100 mL) and dried over sodium sulphate. The organic phase was concentrated under vacuum to obtain the crude residue, which was further purified by flash chromatography using methanol:triethylamine:chloroform in the ratio of 1:1:98 to afford the title compound (34 grams).

Yield: 74%.

$^1$H-NMR (δ ppm): 1.47 (9H, s), 1.76-1.81 (2H, m), 1.90-1.95 (2H, m), 3.32-3.39 (2H, m), 3.62-3.79 (10H, m), 4.49-4.55 (1H, m), 6.69-6.73 (1H, d, J=15.92 Hz), 6.88-6.94 (2H, d, J=8.64 Hz); 7.45-7.49 (2H, d, J=8.64 Hz), 7.64-7.68 (1H, d, J=15.92);

Mass (m/z): 417.3 (M+H)$^+$.

Step (iv): Preparation of 3-[4-(Piperidin-4-yloxy) phenyl]-1-(morpholin-4-yl)prop-2-ene-1-one A solution of 3-[4-(1-t-Butyloxycarbonyl piperidin-4-yloxy)phenyl]-1-(morpholin-4-yl)prop-2-ene-1-one (29.8 grams, 0.071 moles) in dichloromethane (400 mL) was treated with trifluoroacetic acid (55.6 mL, 0.726 moles) at room temperature. The reaction mass was stirred for 6 hours at room temperature. The progress of the reaction was monitored by thin layer chromatography. After completion of the reaction, the reaction mass was poured on to chilled water (500 mL) and basified with 40% lye solution (pH~9). The layers were separated and the aqueous layer was extracted with dichloromethane (2×200 mL) and the combined organic phase was washed with water (150 mL), brine solution (150 mL) and dried over sodium sulphate. The organic phase was concentrated on rotavacuum to afford the title compound (21.2 grams).

Yield: 90%.

$^1$H-NMR (δ ppm): 1.63-1.72 (2H, m), 2.00-2.04 (2H, m), 2.71-2.77 (2H, m), 3.12-3.18 (2H, m), 3.73 (8H, m), 4.39-

4.44 (1H, m), 6.69-6.73 (1H, d, J=15.32 Hz), 6.89-6.91 (2H, d, J=8.64 Hz); 7.45-7.47 (2H, d, J=8.64 Hz), 7.64-7.68 (1H, d, J=15.32 Hz);

Mass (m/z): 317.3 (M+H)+.

Preparation 2: Preparation of 1-(Morpholin-4-yl)-3-[2-(piperidin-4-yloxy)pyridin-5-yl]-prop-2-ene-1-one Step (i): Preparation of t-Butyl 4-(5-bromo pyridin-2-yloxy)piperidine-1-carboxylate To a stirred solution of sodium hydride (4.0 grams, 60% dispersion in mineral oil, 0.1 moles) in tetrahydrofuran (50 mL) was added t-butyl 4-hydroxy piperidine-1-carboxylate (15 grams, 0.075 moles) in tetrahydrofuran (50 mL) at 10° C. under nitrogen atmosphere. The mass was stirred for 1 hour at room temperature. A solution of 2,5-dibromo pyridine (11.8 grams, 0.05 moles) in tetrahydrofuran (50 mL) was added drop wise to the above reaction mass at room temperature and stirred for 4 hours at 65° C. The progress of the reaction was monitored by thin layer chromatography. After completion of reaction, the mass was quenched on to chilled water (600 mL) and the compound was extracted with ethyl acetate (3×200 mL). The resulting organic layer was washed with water, dried over sodium sulfate and concentrated under vacuum. The residue, thus obtained, was purified by flash chromatography using ethyl acetate:n-hexane in the ratio of 1:9 to afford the title compound (15 grams).

Yield: 84%.

$^1$H-NMR (δ ppm): 1.47 (9H, s), 1.68-1.74 (2H, m), 1.91-2.00 (2H, m), 3.24-3.31 (2H, m), 3.72-3.78 (2H, m), 5.14-5.18 (1H, m), 6.62-6.64 (1H, d, J=8.78 Hz), 7.62-7.65 (1H, dd, J=8.76 & 2.57 Hz), 8.15-8.16 (1H, d, J=2.48 Hz);

Mass (m/z): 357.1, 359.2 (M+H)+.

Step (ii): Preparation of 3-[2-(1-t-Butyloxycarbonyl piperidin-4-yloxy)pyridin-5-yl]-1-(morpholin-4-yl)prop-2-ene-1-one A solution of t-butyl 4-(5-bromo pyridin-2-yloxy)piperidine-1-carboxylate (1 gram, 2.80 mmoles), 4-acryloylmorpholine (0.63 gram, 4.46 mmoles), palladium acetate (13 mg, 0.061 mmoles) tri(o-tolyl)phosphine (25.6 mg, 0.084 mmoles) and potassium carbonate (0.62 g, 4.49 mmoles) in DMF (15 mL) was stirred for 3 hours at 140° C. The progress of the reaction was monitored by thin layer chromtography. After completion of reaction, the mass was quenched on to chilled water (30 mL) and the product was extracted with ethyl acetate (3×15 mL). The resulting organic layer was washed with water, dried over sodium sulfate and concentrated under vacuum. The residue, thus obtained, was purified by flash chromatography using ethyl acetate:n-hexane in the ratio of 1:1 to afford the title compound (1.07 grams).

Yield: 80%.

$^1$H-NMR (δ ppm): 1.47 (9H, s), 1.72-1.76 (2H, m), 1.98-2.03 (2H, m), 3.26-3.32 (2H, m), 3.58-3.80 (10H, m), 5.23-5.27 (1H, m), 6.33-6.37 (1H, d, J=15.96 Hz), 6.72-6.76 (1H, m), 7.62-7.67 (1H, m), 7.76-7.79 (1H, m), 8.24-8.25 (1H, m);

Mass (m/z): 418.3 (M+H)+.

Step (iii): Preparation of 1-(Morpholin-4-yl)-3-[2-(piperidin-4-yloxy)pyridin-5-yl]-prop-2-ene-1-one A solution of 3-[2-(1-t-Butyloxycarbonyl piperidin-4-yloxy)pyridin-5-yl]-1-(morpholin-4-yl)prop-2-ene-1-one (0.7 grams, 0.0016 moles) in dichloromethane (20 mL) was treated with trifluoroacetic acid (1.3 mL, 0.016 moles) at room temperature. The reaction mass was stirred for 6 hours at room temperature. The progress of the reaction was monitored by thin layer chromatography. After completion of reaction, the reaction mass was poured on to chilled water (30 mL) and basified with 40% lye solution (pH~9). The layers were separated and the aqueous layer was further extracted with dichloromethane (2×20 mL). The combined organic phase was washed with water (30 mL), brine solution (30 mL) and dried over sodium sulphate. The organic phase was concentrated on rotavacuum to afford the title compound (0.48 grams).

Yield: 90%.

$^1$H-NMR (δ ppm): 1.72-1.76 (2H, m), 1.98-2.03 (2H, m), 3.26-3.32 (2H, m), 3.58-3.80 (10H, m), 5.23-5.27 (1H, m), 6.33-6.37 (1H, d, J=15.96 Hz), 6.72-6.76 (2H, m), 7.62-7.67 (1H, m), 7.76-7.79 (1H, m), 8.24-8.25 (1H, m); Mass (m/z): 318.3 (M+H)+.

Example 1

Preparation of 3-[4-(1-Cyclobutyl piperidin-4-yloxy)phenyl]-1-(morpholin-4-yl)prop-2-ene-1-one fumarate salt Step (i): Preparation of 3-[4-(1-Cyclobutyl piperidin-4-yloxy)phenyl]-1-(morpholin-4-yl)prop-2-ene-1-one Sodium triacetoxyborohydride (38.6 grams, 0.18 moles) was added in a single lot to a well stirred solution of 3-[4-(Piperidin-4-yloxy)phenyl]-1-(morpholin-4-yl)prop-2-ene-1-one (19.1 grams, 0.060 moles, obtained in preparation 1) and cyclobutanone (6.8 mL, 0.09 moles) in dichloroethane (500 mL). The mixture was further stirred at room temperature for 6 hours. The progress of the reaction was monitored by thin layer chromatography. After completion of reaction, the mass was quenched on to water (1000 mL) and basified with 40% lye solution (pH~9). The layers were separated and the aqueous layer was extracted with dichloromethane (2×200 mL). The combined organic layer was washed with brine solution (250 mL), dried over sodium sulfate, concentrated under vacuum and the residual mass was further purified by flash chromatography using methanol:triethylamine:chloroform in the ratio of 1.5:0.25:98.25 to obtain the title compound (17.4 grams).

Yield: 77%.

$^1$H-NMR (δ ppm): 1.68-1.73 (2H, m), 1.80-1.95 (4H, m), 1.99-2.06 (4H, m), 2.19-2.24 (2H, m), 2.55-2.62 (2H, m), 2.70-2.79 (1H, m), 3.60-3.88 (8H, m), 4.29-4.35 (1H, m), 6.68-6.72 (1H, d), 6.88-6.93 (2H, m); 7.44-7.49 (2H, m), 7.64-7.68 (1H, d);

Mass (m/z): 371.1 (M+H)+.

Step (ii): Preparation of 3-[4-(1-Cyclobutyl piperidin-4-yloxy)phenyl]-1-(morpholin-4-yl)prop-2-ene-1-one fumarate salt To a stirred solution of 3-[4-(1-Cyclobutyl piperidin-4-yloxy)phenyl]-1-(morpholin-4-yl)prop-2-ene-1-one (23.52 grams, 0.063 moles) in methanol (300 mL) was added a solution of fumaric acid (7.32 grams, 0.063 moles) in 30 mL methanol. The clear mass, thus obtained, was further stirred for 2-3 hours at room temperature. The solvent was evaporated to afford a solid mass. The solid mass was triturated with diethyl ether (3×100 mL) and dried under reduced pressure to obtain the title compound (29.54 grams).

Yield: 95%.

1H-NMR (δ ppm): 1.60-1.65 (2H, m), 1.73-1.77 (2H, m), 2.01-2.09 (6H, m), 2.49-2.52 (2H, m), 2.81-2.89 (2H, m), 3.14-3.19 (1H, m), 3.50-3.70 (8H, m), 4.50-4.60 (1H, m), 6.56 (2H, s), 6.97-6.99 (2H, d, J=8.45 Hz), 7.07-7.10 (1H, d, J 15.32 Hz), 7.43-7.47 (1H, d, J=15.27 Hz), 7.63-7.65 (2H, d, J=8.45 Hz);

Mass (m/z): 371.3 (M+H)$^+$.

Examples 2-28

The compounds of Examples 2-28 were prepared by following the procedures as described in Example 1, with some non-critical variations

| | | |
|---|---|---|
| 2. | 3-[4-(1-Cyclobutyl piperidin-4-yloxy)phenyl]-1-(piperidin-1-yl)prop-2-ene-1-one hydrochloride salt | $^1$H-NMR (δ ppm): 1.60-1.74 (8H, m), 1.82-1.87 (2H, m), 1.95-2.08 (6H, m), 2.29 (2H, bs), 2.64 (2H, bs), 2.78-2.82 (1H, m), 3.62-3.65 (4H, m), 4.39 (1H, m), 6.75-6.79 (1H, d, J = 15.3 Hz), 6.87-6.89 (2H, d, J = 8.63 Hz), 7.44-7.46 (2H, d, J = 8.63 Hz), 7.58-7.62 (1H, d, J = 15.3 Hz); Mass (m/z): 369.3 (M + H)$^+$. |
| 3. | 3-[4-(1-Cyclobutyl piperidin-4-yloxy)phenyl]-1-(1,1-dioxo thiomorpholin-4-yl)prop-2-ene-1-one hydrochloride salt | $^1$H-NMR (δ ppm): 1.66-1.97 (6H, m), 2.07 (5H, s), 2.25 (2H, bs), 2.63 (2H, bs), 2.76-2.80 (1H, m), 2.86-2.89 (1H, m), 3.10 (4H, m), 4.17 (4H, m), 4.40 (1H, bs), 6.69-6.73 (1H, d, J = 15.2 Hz), 6.89-6.91 (2H, d, J = 8.65 Hz), 7.46-7.48 (2H, d, J = 8.66 Hz), 7.69-7.73 (1H, d, J = 15.2 Hz); Mass (m/z): 419.2 (M + H)$^+$. |
| 4. | 3-[2-(1-Cyclobutyl piperidin-4-yloxy)pyridin-5-yl]-1-(piperidin-1-yl)prop-2-ene-1-one L(+)-Tartarate salt | $^1$H-NMR (δ ppm): 1.66-1.72 (8H, m), 1.80-1.85 (2H, m), 1.95-2.03 (6H, m), 2.32 (2H, bs), 2.63 (2H, bs), 2.80-2.82 (1H, m), 2.88 (2H, s) 3.60-3.63 (4H, m), 3.82 (1H, m), 5.30-5.32 (1H, d , J = 8.36 Hz), 5.55-5.59 (1H, d, J = 15.6 Hz), 5.94-5.98 (1H, d, J = 15.6 Hz), 6.52-6.54 (1H, d, J = 8.32 Hz), 6.75 (1H, s); Mass (m/z): 370.4 (M + H)$^+$. |
| 5. | 3-[2-(1-Cyclobutyl piperidin-4-yloxy)pyridin-5-yl]-1-(morpholin-4-yl)prop-2-ene-1-one L(+)-Tartarate salt | $^1$H-NMR (δ ppm): 1.68-1.75 (2H, m), 1.80-1.95 (4H, m), 1.99-2.06 (4H, m), 2.19-2.24 (2H, m), 2.55-2.62 (2H, m), 2.70-2.79 (1H, m), 2.87 (2H, s), 3.60-3.88 (8H, m), 5.42 (1H, m), 6.93-6.99 (1H, m), 7.09-7.13 (1H, m), 7.55-7.58 (1H, m), 8.08-8.10 (1H, m), 8.32 (1H, s); Mass (m/z): 372.4 (M + H)$^+$. |
| 6. | 3-[2-Fluoro-4-(1-isopropyl piperidin-4-yloxy)phenyl]-1-(morpholin-4-yl)prop-2-ene-1-one L(+)-Tartarate salt | $^1$H-NMR (δ ppm): 1.16-1.18 (2H, m), 1.20-1.27 (1H, m), 1.38-1.41 (6H, m), 1.90-2.34 (4H, m), 3.30-3.69 (4H, m), 3.71-3.80 (7H, m), 4.53 (2H, m), 6.80-6.89 (2H, m), 7.06-7.10 (1H, m), 7.67-7.71 (2H, m); Mass (m/z): 377.3 (M + H)$^+$. |
| 7. | 3-[2-Fluoro-4-(1-cyclobutyl piperidin-4-yloxy)phenyl]-1-(morpholin-4-yl)prop-2-ene-1-one L(+)-Tartarate salt | 1$^1$H-NMR (δ ppm): 1.60-1.70 (4H, m), 1.80-1.90 (2H, m), 1.99-2.09 (3H, m), 2.14-2.20 (2H, m), 2.40-2.51 (4H, m), 2.70-2.76 (2H, m), 3.00-3.09 (1H, m), 3.48 (2H, s), 3.60-3.80 (6H, m), 4.53 (2H, m), 6.61-6.70 (2H, m), 6.85-6.89 (1H, d , J = 15.56 Hz), 7.39-7.43 (1H, m), 7.65-7.69 (1H, d, J = 15.56 Hz); Mass (m/z): 389.4 (M + H)$^+$. |
| 8. | 3-[4-(1-Cyclobutyl piperidin-4-yloxy)-2-methyl phenyl]-1-(morpholin-4-yl)prop-2-ene-1-one L(+)-Tartarate salt | $^1$H-NMR (δ ppm): 1.81-1.91 (3H, m), 2.11-2.33 (9H, m), 2.41 (3H, s), 3.14-3.20 (4H, m), 3.71 (8H, s), 4.43 (2H, s), 6.85-6.93 (3H, m), 7.67-7.69 (1H, d , J = 8.3 Hz), 7.85-7.89 (1H, d, J = 15. Hz); Mass (m/z): 385.4 (M + H)$^+$. |
| 9. | 3-[4-(1-Isopropyl piperidin-4-yloxy)-2-methyl phenyl]-1-(morpholin-4-yl)prop-2-ene-1-one L(+)-Tartarate salt | $^1$H-NMR (δ ppm): 1.38-1.40 (6H, d), 1.91-1.98 (1H, m), 2.16-2.30 (4H, m), 2.42 (3H, s), 3.34-3.57 (3H, m), 3.71 (8H, s), 4.41 (2H, s), 4.75 (2H, m), 6.86-6.95 (3H, m), 7.69-7.71 (1H, d, J = 8.45 Hz), 7.86-7.90 (1H, d, J = 15.28 Hz) Mass (m/z): 373.4 (M + H)$^+$. |
| 10. | 3-[4-(1-Cyclobutyl piperidin-4-yloxy)phenyl]-1-(morpholin-4-yl)prop-2-ene-1-one L(+)-Tartarate salt | $^1$H-NMR (δ ppm): 1.60-1.65 (2H, m), 1.73-1.77 (2H, m), 2.01-2.09 (6H, m), 2.49-2.52 (2H, m), 2.81-2.89 (2H, m), 3.14-3.19 (1H, m), 3.50-3.70 (8H, m), 4.46 (2H, s), 4.50-4.60 (1H, m), 6.97-6.99 (2H, d, J = 8.45 Hz), 7.07-7.10 (1H, d, J = 15.32 Hz), 7.43-7.47 (1H, d, J = 15.27 Hz), 7.63-7.65 (2H, d, J = 8.45 Hz); Mass (m/z): 371.3 (M + H)$^+$. |
| 11. | 3-[4-(1-Cyclobutyl piperidin-4-yloxy)-3-methoxy phenyl]-1-(morpholin-4-yl)prop-2-ene-1-one L(+)-Tartarate salt | $^1$H-NMR (δ ppm): 1.86-1.93 (3H, m), 2.14-2.38 (9H, m), 3.15-3.25 (3H, m), 3.72 (8H, s), 3.92 (3H, s), 4.46 (2H, s), 4.71-4.77 (1H, m), 7.06-7.10 (2H, m), 7.19-7.21 (1H, d, J = 7.7 Hz), 7.35 (1H, s), 7.54-7.58 (1H, d, J = 15.37 Hz); Mass (m/z): 401.3 (M + H)$^+$. |
| 12. | 3-[4-(1-Cyclopropylmethyl piperidin-4-yloxy)-3-methoxy phenyl]-1-(morpholin-4-yl)prop-2-ene-1-one L(+)-Tartarate salt | $^1$H-NMR (δ ppm): 0.46-0.48 (2H, m), 0.78-0.83 (2H, m), 1.15-1.19 (1H, m), 1.33-1.39 (2H, m), 2.17-2.26 (4H, m) 3.07-3.10 (2H, m), 3.41-3.52 (2H, m) 3.72 (8H, s), 3.92 (3H, s), 4.46 (2H, s), 4.69 (1H, m), 7.05-7.09 (2H, m), 7.20-7.22 (1H, d, J = 8.2 Hz), 7.35 (1H, s), 7.54-7.58 (1H, d, J = 15.37 Hz); Mass (m/z): 401.4 (M + H)$^+$. |
| 13. | 3-[4-(1-Isobutyl piperidin-4-yloxy)-3-methoxy phenyl]-1-(morpholin-4-yl)prop-2-ene-1-one L(+)-Tartarate salt | $^1$H-NMR (δ ppm): 1.03-1.05 (6H, d), 2.13-2.15 (5H, m), 2.96-2.98 (2H, m), 3.39-3.45 (4H, m), 3.68-3.81 (8H, m), 3.88 (3H, s), 4.39 (2H, s), 4.65 (1H, m), 7.05-7.09 (2H, m), 7.15-7.17 (1H, d, J = 8.28 Hz), 7.31 (1H, s), 7.50-7.54 (1H, d, J = 15.36 Hz); Mass (m/z): 403.4 (M + H)$^+$. |
| 14. | 3-[4-(1-Isopropyl piperidin-4-yloxy)-3-methoxy phenyl]-1-(morpholin-4-yl)prop-2-ene-1- | $^1$H-NMR (δ ppm): 1.40-1.42 (6H, d), 1.92-1.96 (1H, m), 2.14-2.31 (4H, m), 3.48-3.49 (4H, m), 3.72-3.93 (8H, s), 3.93 (3H, s), 4.44 (2H, s), 4.80-4.82 (1H, m), 7.06-7.10 (2H, |

| | | |
|---|---|---|
| | one L(+)-Tartarate salt | m), 7.20-7.22 (1H, d, J = 7.76 Hz), 7.35 (1H, s) 7.54-7.58 (1H, d, J = 15.37 Hz); Mass (m/z): 389.4 (M + H)+. |
| 15. | 3-[4-(1-Isopropyl piperidin-4-yloxy)-3-methoxy phenyl]-1-(piperidin-1-yl)prop-2-ene-1-one L(+)-Tartarate salt | 1H-NMR (δ ppm): 1.36-1.38 (6H, d), 1.60-1.62 (4H, m), 1.69-1.70 (2H, m), 2.14 (4H, bs), 3.44-3.46 (4H, m), 3.53-3.56 (1H, m), 3.63-3.75 (4H, m), 3.89 (3H, s), 4.39 (2H, s), 4.64-4.66 (1H, m), 7.03-7.07 (2H, m), 7.14-7.16 (1H, d, J= 8.21 Hz), 7.29 (1H, s), 7.45-7.49 (1H, d, J = 15.53 Hz); Mass (m/z): 387.4 (M + H)+. |
| 16. | 3-[4-(1-Cyclobutyl piperidin-4-yloxy)-3-methoxy phenyl]-1-(piperidin-1-yl)prop-2-ene-1-one L(+)-Tartarate salt | 1H-NMR (δ ppm): 0.46-0.48 (2H, m), 0.81-0.83 (2H, m), 1.18-1.21 (2H, m), 1.34-1.30 (2H, d, J = 6.56 Hz), 1.62-1.64 (4H, m), 1.73-1.75 (2H, m), 2.18 (4H, bs), 3.08-3.10 (2H, m), 3.39-3.50 (1H, m), 3.67-3.73 (4H, m), 3.93 (3H, s), 4.45 (2H, s), 4.70-4.76 (1H, m), 7.07-7.11 (2H, m), 7.18-7.20 (1H, d, J = 8.23 Hz), 7.34 (1H, s), 7.49-7.53 (1H, d, J = 15.38 Hz); Mass (m/z): 399.5 (M + H)+. |
| 17. | 3-[4-(1-Cyclopropylmethyl piperidin-4-yloxy)phenyl]-1-(morpholin-4-yl)prop-2-ene-1-one | 1H-NMR (δ ppm): 0.09-0.12 (2H, d), 0.50-0.54 (2H, d), 0.85-0.89 (1H, m), 1.81-1.90 (2H, m), 2.01-2.05 (2H, m), 2.27-2.28 (2H, d), 2.38-2.41 (2H, m), 2.83-2.89 (2H, m), 3.62-3.72 (8H, m), 4.35-4.37 (1H, m), 6.68-6.72 (1H, d , J = 15.30 Hz), 6.88-6.90 (2H, m, J = 8.64 Hz), 7.44-7.46 (2H, m, J = 8.63 Hz), 7.63-7.67 (1H, d , J = 15.33 Hz); Mass (m/z): 371.2 (M + H)+. |
| 18. | 3-[4-(1-Isobutyl piperidin-4-yloxy)phenyl]-1-(morpholin-4-yl)prop-2-ene-1-one | 1H-NMR (δ ppm): 0.89-0.90 (6H, d), 1.73-1.84 (3H, m), 1.97-2.00 (2H, m), 2.08-2.10 (2H, d), 2.18-2.23 (2H, m), 2.68-2.70 (2H, m), 3.62-3.72 (8H, m), 4.31-4.35 (1H, m), 6.68-6.71 (1H, d, J = 15.38 Hz), 6.87-6.89 (2H, m, J = 8.62 Hz), 7.44-7.46 (2H, m, J = 8.65 Hz), 7.63-7.67 (1H, d, J = 15.30 Hz); Mass (m/z): 373.4 (M + H)+. |
| 19. | 3-[3-Bromo-4-(1-isopropyl piperidin-4-yloxy)phenyl]-1-(morpholin-4-yl)prop-2-ene-1-one | 1H-NMR (δ ppm): 1.25-1.27 (6H, d), 2.01-2.06 (1H, m), 2.11-2.14 (2H, m), 2.61-2.68 (2H, m), 3.11-3.18 (2H, m), 3.23-3.27 (2H, m), 3.66-3.73 (8H, m), 4.79-4.80 (1H, m), 6.71-6.75 (1H, d, J = 15.32 Hz), 6.90-6.92 (1H, d, J = 8.50 Hz), 7.42-7.44 (1H, dd, J = 8.49 Hz), 7.56-7.60 (1H, d, J = 15.33 Hz) 7.74 (1H, d, J = 1.56 Hz); Mass (m/z): 437.3, 439.2 (M + H)+. |
| 20. | 3-[3-Bromo-4-(1-cyclobutyl piperidin-4-yloxy)phenyl]-1-(morpholin-4-yl)prop-2-ene-1-one | 1H-NMR (δ ppm): 1.37-1.42 (2H, m), 1.57-1.61 (2H, m), 1.68-1.75 (2H, m), 1.84 (1H, m), 2.01-2.04 (2H, m), 2.13-2.15 (2H, m), 2.31-2.32 (2H, m), 2.75-2.80 (2H, m), 3.66-3.72 (8H, m), 4.66-4.70 (1H, m), 6.69-6.73 (1H, d , J = 15.37 Hz), 6.88-6.90 (1H, d, J = 8.57 Hz), 7.38-7.41 (1H, dd, J = 8.34, 1.44 Hz), 7.56-7.60 (1H, d , J = 15.33 Hz) 7.74 (1H, d, J = 1.77 Hz); Mass (m/z): 449.3, 451.2 (M + H)+. |
| 21. | 3-[3-Bromo-4-(1-isobutyl piperidin-4-yloxy)phenyl]-1-(morpholin-4-yl)prop-2-ene-1-one | 1H-NMR (δ ppm): 1.25-1.27 (6H, d), 1.62-1.71 (4H, m), 1.94-1.99 (2H, m), 2.01-2.06 (1H, m), 2.21-2.39 (2H, m), 2.76-2.80 (2H, m), 3.67-3.72 (8H, m), 4.50-4.53 (1H, m), 6.69-6.72 (1H, d, J = 15.36 Hz), 6.87-6.90 (1H, d, J = 8.55 Hz), 7.36-7.38 (1H, d, J = 8.39 Hz), 7.56-7.60 (1H, d, J = 15.35 Hz), 7.75 (1H, d, J = 1.86 Hz); Mass (m/z): 451.2, 453.3 (M + H)+. |
| 22. | 3-[3-Bromo-4-(1-cyclopropylmethyl piperidin-4-yloxy)phenyl]-1-(morpholin-4-yl)prop-2-ene-1-one | 1H-NMR (δ ppm): 0.29-0.31 (2H, d), 0.66-0.68 (2H, d), 1.11-1.15 (1H, m), 2.05-2.08 (2H, m), 2.38-2.42 (2H, m), 2.62-2.70 (2H, m), 3.03-3.10 (4H, m), 3.66-3.72 (8H, m), 4.68-4.71 (1H, m), 6.70-6.73 (1H, d, J = 15.33 Hz), 6.89-6.91 (1H, d, J = 8.55 Hz), 7.39-7.41 (1H, d, J = 8.46 Hz), 7.56-7.60 (1H, d, J = 15.31 Hz) 7.74-7.75 (1H, d, J = 1.60 Hz); Mass (m/z): 449.3, 451.2 (M + H)+. |
| 23. | 3-[6-(1-Cyclopropylmethyl piperidin-4-yloxy)pyridin-3-yl]-1-(morpholin-4-yl)prop-2-ene-1-one L(+)-Tartarate salt | 1H-NMR (δ ppm): 0.44-0.47 (2H, m), 0.76-0.81 (2H, m), 1.16-1.19 (1H, m), 1.28-1.30 (1H, m), 2.19-2.30 (4H, m), 3.06-3.08 (2H, d), 3.35-3.49 (3H, bs), 3.72-3.76 (8H, m), 4.42 (2H, s), 5.39 (1H, bs), 6.88-6.90 (1H, d, J = 8.64 Hz), 7.10-7.14 (1H, d, J = 15.46 Hz), 7.56-7.60 (1H, d, J = 15.46 Hz), 8.09-8.11 (1H, dd, J = 8.61, 2.21 Hz), 8.34-8.35 (1H, d, J = 2 Hz); Mass (m/z): 372.4 (M + H)+. |
| 24. | 3-[6-(1-Isobutyl piperidin-4-yloxy)pyridin-3-yl]-1-(morpholin-4-yl)prop-2-ene-1-one L(+)-Tartarate salt | 1H-NMR (δ ppm): 1.08-1.09 (6H, d), 1.28-1.30 (1H, m), 1.39-1.42 (1H, m), 2.18-2.31 (4H, m), 3.03-3.05 (2H, d), 3.35-3.49 (3H, m), 3.72-3.76 (8H, m), 4.47 (2H, s), 5.40 (1H, bs), 6.88-6.90 (1H, d, J = 8.59 Hz), 7.11-7.15 (1H, d, J = 15.46 Hz), 7.56-7.60 (1H, d, J = 15.46 Hz), 8.09-8.12 (1H, dd, J = 8.52, 1.86 Hz), 8.34-8.35 (1H, d, J = 1.86 Hz); Mass (m/z): 374.4 (M + H)+. |

-continued

| | | |
|---|---|---|
| 25. | 3-[2-Chloro-4-(1-cyclobutyl piperidin-4-yloxy)phenyl]-1-(morpholin-4-yl)prop-2-ene-1-one | $^1$H-NMR (δ ppm): 1.69-1.76 (4H, d), 1.82-1.94 (3H, m), 2.00-2.09 (3H, m), 2.21-2.25 (2H, m), 2.59-2.63 (2H, m), 2.73-2.79 (1H, m), 3.70-3.76 (8H, m), 4.11-4.16 (1H, bs), 6.74-6.78 (1H, d, J = 15.41 Hz), 6.82-6.85 (1H, dd, J = 8.71, 2.2 Hz), 6.97-6.98 (1H, d, J = 2.23 Hz), 7.53-7.55 (1H, dd, J = 8.71 Hz), 7.99-8.03 (1H, d, J = 15.42 Hz); Mass (m/z): 405.3, 407.4 (M + H)$^+$. |
| 26. | 3-[2-Chloro-4-(1-isopropyl piperidin-4-yloxy)phenyl]-1-(morpholin-4-yl)prop-2-ene-1-one | $^1$H-NMR (δ ppm): 1.05-1.06 (6H, d), 1.78-1.85 (2H, m), 1.99-2.09 (2H, m), 2.38-2.43 (2H, t), 2.72-2.78 (3H, m), 3.66-3.72 (8H, s), 4.30-4.33 (1H, m), 6.71-6.74 (1H, d, J = 15.33 Hz), 6.79-6.81 (1H, dd, J = 8.71, 2.07 Hz), 6.94-6.95 (1H, d, J = 2.4 Hz), 7.49-7.52 (1H, d, J = 8.73 Hz), 7.96-7.99 (1H, d, J = 15.39 Hz); Mass (m/z): 393.2, 395.2 (M + H)$^+$. |
| 27. | 3-[2-Chloro-4-(1-cyclopropylmethyl piperidin-4-yloxy)phenyl]-1-(morpholin-4-yl)prop-2-ene-1-one | $^1$H-NMR (δ ppm): 0.13-0.19 (2H, m), 0.54-0.59 (2H, m), 0.90-0.91 (1H, m), 1.87-1.93 (2H, m), 2.04-2.09 (2H, m), 2.31-2.32 (2H, d), 2.43 (2H, m), 2.86 (2H, m), 3.69-3.76 (8H, m), 4.37-4.38 (1H, m), 6.74-6.78 (1H, d, J = 15.41 Hz), 6.83-6.86 (1H, dd, J = 8.72, 2.22 Hz), 6.98-6.99 (1H, d, J = 2.41 Hz), 7.54-7.56 (1H, d, J = 8.71 Hz), 8.00-8.03 (1H, d, J = 15.46 Hz); Mass (m/z): 405.3, 407.4 (M + H)$^+$. |
| 28. | 3-[2-Chloro-4-(1-isobutyl piperidin-4-yloxy)phenyl]-1-(morpholin-4-yl)prop-2-ene-1-one | $^1$H-NMR (δ ppm): 0.93-0.94 (6H, d), 1.77-1.87 (3H, m), 2.00-2.04 (2H, m), 2.12-2.14 (2H, d), 2.23-2.28 (2H, t), 2.72 (2H, m), 3.70-3.76 (8H, s), 4.32-4.36 (1H, m), 6.74-6.78 (1H, d, J = 15.45 Hz), 6.82-6.85 (1H, dd, J = 8.72, 2.35 Hz), 6.97-6.98 (1H, d, J = 2.24 Hz), 7.53-7.55 (1H, d, J = 8.76 Hz), 8.00-8.03 (1H, d, J = 15.41 Hz); Mass (m/z): 407.3, 409.2 (M + H)$^+$. |

Biological Assays

Example 29

Binding and Functional Assays for Human or Rat Histamine H3 Receptor

Compounds can be evaluated according to the following procedures.

Materials and Methods:
  Receptor source: Rat brain frontal cortex or recombinant human cDNA expressed in CHO cells
  Radioligand: [$^3$H] R-α-methylhistamine
  Final ligand concentration—[3.0 nM]
  Non-specific determinant: R-α-methylhistamine (100 μM)
  Reference compound: R-α-methylhistamine
  Positive control: R-α-methylhistamine Incubation Conditions:

Increasing concentrations of test compounds or standard were incubated with membrane receptors and radioligand in 5 mM MgCl$_2$ and 50 mM TRIS-HCl (pH 7.4) for 60 minutes at room temperature. The reaction was terminated by rapid vacuum filtration onto the glass fiber filters. Radioactivity trapped onto the filters was determined and compared to the control values in order to ascertain any interactions of the test compound(s) with either cloned human or rat receptor binding site.

| Example Number | $K_i$ (nM) |
|---|---|
| 1. | 1.32 |
| 2. | 1.82 |
| 3. | 1.40 |
| 4. | 7.82 |
| 5. | 7.90 |
| 6. | 17.49 |
| 7. | 2.96 |
| 8. | 6.34 |
| 9. | 13.10 |

-continued

| Example Number | $K_i$ (nM) |
|---|---|
| 10. | 3.43 |
| 11. | 77.18 |
| 18. | 32.35 |
| 19. | 16.97 |
| 20. | 5.97 |
| 22. | 52.62 |
| 25. | 29.71 |

Example 30

Rodent Pharmacokinetic Study

Male Wistar rats (230-280 grams) were used as experimental animals. Three to five animals were housed in each cage. One day prior to dosing day, male wistar rats (225-250 grams) were anesthetized with isoflurane for surgical placement of jugular vein catheter. Animals were kept fasted over night and maintained on a 12 hours light/dark cycle. Three rats were dosed with compounds of formula (I) orally (3 mg/Kg) and intravenously (1 mg/kg) in two separate set of animals (n=3 rats/group).

At each time point, blood was collected by jugular vein. Blood was stored frozen at 4° C. until analysis. The concentrations of the compounds of formula (I) in blood were determined using LC-MS/MS method. Schedule time points: Pre dose 0.08 (only for i.v.) 0.25, 0.5, 1, 2, 4, 6, 8, and 24 hours after dosing (n=3). The compounds of formula (I) were quantified in blood by validated LC-MS/MS method using acetonitrile precipitation technique. The compounds of formula (I) were quantified in the calibration range of 1-1000 ng/mL in blood. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using software Pheonix WinNonlin version 6.0.1.

| Example Number | Strain/ Sex | Dose (mg/kg) | Vehicle | Route of administration | $C_{max}$ (ng/mL) | $T_{max}$ (h) | $AUC_t$ (ng·hr/mL) | $T_{1/2}$ (h) | Bioavailability (%) |
|---|---|---|---|---|---|---|---|---|---|
| 1. | Wistar rats/Male | 3 | Reagent grade water | Per-Oral | 106 ± 5 | 0.50 ± 0.00 | 176 ± 10 | 1.56 ± 0.43 | 29 ± 2 |
|  |  | 1 | Sterile water for injection | Intravenous | 214 ± 25 | 0.08 ± 0.00 | 208 ± 7 | 1.05 ± 0.07 |  |
| 5. | Wistar rats/Male | 3 | Reagent grade water | Per-Oral | 128 ± 6 | 0.42 ± 0.14 | 184 ± 25 | 1.1 ± 0.3 | 35 ± 5 |
|  |  | 1 | Sterile water for injection | Intravenous | 220 ± 10 | 0.08 ± 0.00 | 173 ± 13 | 0.6 ± 0.20 |  |
| 7. | Wistar rats/Male | 3 | Reagent grade water | Per-Oral | 57 ± 36 | 0.25 ± 0.00 | 49 ± 29 | 0.9 ± 0.6 | 9 ± 5 |
|  |  | 1 | Sterile water for injection | Intravenous | 311 ± 110 | 0.08 ± 0.00 | 167 ± 47 | 0.6 ± 0.2 |  |
| 10. | Wistar rats/Male | 3 | Reagent grade water | Per-Oral | 290 ± 32 | 0.25 ± 0.00 | 387 ± 38 | 0.85 ± 0.14 | 58 ± 6 |
|  |  | 1 | Sterile water for injection | Intravenous | 285 ± 46 | 0.08 ± 0.00 | 222 ± 33 | 0.80 ± 0.05 |  |

Example 31

Rodent Brain Penetration Study

Male Wistar rats (230-280 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male wistar rats (225-250 grams) were acclimatized. After acclimatization, the rats were grouped according to the weight in each group, 3 animals were kept in individual cage and allowed free access to food and water. At each time point (05, 1, and 2 hrs) n=3 animals were used.

The compounds of formula (I) were dissolved in water and administered orally at (free base) 3 mg/kg. Blood samples were removed via, cardiac puncture by using light ether anesthesia the animals were sacrificed to collect brain tissue. Brain samples were homogenized and stored frozen at −20° C. until analysis. The concentrations of the compounds of formula (I) in blood and brain were determined using LC-MS/MS method.

The compounds of formula (I) were quantified in blood and brain homogenate by validated LC-MS/MS method using acetonitrile precipitation technique. The compounds of formula (I) were quantified in the calibration range of 1-1000 ng/mL in blood and brain homogenate. Study samples were analyzed using calibration samples in the batch and quality control samples spread across the batch. Extents of brain to blood ratios were calculated ($C_{brain}/C_{blood}$).

| Example Number | Strain/ Sex | Dose (mg/kg) | Vehicle | Route of administration | Brain Penetration @ 1 h post dose ($C_{brain}/C_{blood}$) |
|---|---|---|---|---|---|
| 1. | Wister rats/Male | 3 | Reagent grade water | Per-oral | 1.40 |
| 5. | Wister rats/Male | 3 | Reagent grade water | Per-oral | 0.92 |
| 7. | Wister rats/Male | 3 | Reagent grade water | Per-oral | 2.51 |
| 10. | Wister rats/Male | 3 | Reagent grade water | Per-oral | 1.36 |

Example 32

Object Recognition Task Model

The cognition enhancing properties of compounds of this invention were estimated using a model of animal cognition: the object recognition task model.

Male Wister rats (230-280 grams) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

Some representative compounds have shown positive effects indicating the increased novel object recognition viz; increased exploration time with novel object and higher discrimination index.

| Example Number | Dose mg/kg, p.o. | Exploration time mean ± S.E.M (sec) Familiar object | Novel object | Inference |
|---|---|---|---|---|
| 1. | 1 mg/kg | 5.96 ± 1.03 | 14.86 ± 1.92 | Active |
| 5. | 3 mg/kg | 9.64 ± 2.22 | 15.53 ± 2.36 | Active |

Example 33

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm$^2$ perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition boards that determined path length, swim speed and the number of entries and duration of swim time spent in each quadrant of the water maze.

| Example Number | Reversal of Scopolamine Induced amnesia |
|---|---|
| 10. | 3 & 10 mg/kg, s.c. |

We claim:
1. A compound of the formula (I):

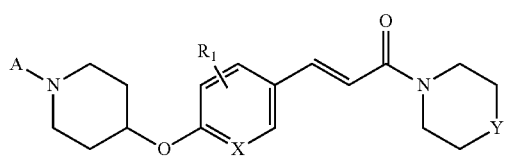

(I)

wherein,
at each occurrence, $R_1$ is independently selected from hydrogen, halogen, alkyl or alkoxy;
"A" is alkyl, cycloalkyl or cycloalkylalkyl;
"X" is CH or N;
"Y" is O or

or its pharmaceutically acceptable salts.
2. The compound according to claim 1, which is selected from the group consisting of:
3-[4-(1-Cyclobutyl piperidin-4-yloxy)phenyl]-1-(morpholin-4-yl) prop-2-ene-1-one fumarate salt;
3-[4-(1-Cyclobutyl piperidin-4-yloxy)phenyl]-1-(1,1-dioxo thiomorpholin-4-yl) prop-2-ene-1-one hydrochloride salt;
3-[2-(1-Cyclobutyl piperidin-4-yloxy)pyridin-5-yl]-1-(morpholin-4-yl) prop-2-ene-1-one L(+)-Tartarate salt;
3-[2-Fluoro-4-(1-isopropyl piperidin-4-yloxy)phenyl]-1-(morpholin-4-yl) prop-2-ene-1-one L(+)-Tartarate salt;
3-[2-Fluoro-4-(1-cyclobutyl piperidin-4-yloxy)phenyl]-1-(morpholin-4-yl) prop-2-ene-1-one L(+)-Tartarate salt;
3-[4-(1-Cyclobutyl piperidin-4-yloxy)-2-methyl phenyl]-1-(morpholin-4-yl) prop-2-ene-1-one L(+)-Tartarate salt;
3-[4-(1-Isopropyl piperidin-4-yloxy)-2-methyl phenyl]-1-(morpholin-4-yl) prop-2-ene-1-one L(+)-Tartarate salt;
3-[4-(1-Cyclobutyl piperidin-4-yloxy)phenyl]-1-(morpholin-4-yl) prop-2-ene-1-one L(+)-Tartarate salt;
3-[4-(1-Cyclobutyl piperidin-4-yloxy)-3-methoxy phenyl]-1-(morpholin-4-yl) prop-2-ene-1-one L(+)-Tartarate salt;
3-[4-(1-Cyclopropylmethyl piperidin-4-yloxy)-3-methoxy phenyl]-1-(morpholin-4-yl) prop-2-ene-1-one L(+)-Tartarate salt;
3-[4-(1-Isobutyl piperidin-4-yloxy)-3-methoxy phenyl]-1-(morpholin-4-yl) prop-2-ene-1-one L(+)-Tartarate salt;
3-[4-(1-Isopropyl piperidin-4-yloxy)-3-methoxy phenyl]-1-(morpholin-4-yl) prop-2-ene-1-one L(+)-Tartarate salt;
3-[4-(1-Cyclopropylmethyl piperidin-4-yloxy)phenyl]-1-(morpholin-4-yl) prop-2-ene-1-one;
3-[4-(1-Isobutyl piperidin-4-yloxy)phenyl]-1-(morpholin-4-yl) prop-2-ene-1-one;
3-[3-Bromo-4-(1-isopropyl piperidin-4-yloxy)phenyl]-1-(morpholin-4-yl) prop-2-ene-1-one;
3-[3-Bromo-4-(1-cyclobutyl piperidin-4-yloxy)phenyl]-1-(morpholin-4-yl) prop-2-ene-1-one;
3-[3-Bromo-4-(1-isobutyl piperidin-4-yloxy)phenyl]-1-(morpholin-4-yl) prop-2-ene-1-one;
3-[3-Bromo-4-(1-cyclopropylmethyl piperidin-4-yloxy)phenyl]-1-(morpholin-4-yl) prop-2-ene-1-one;
3-[6-(1-Cyclopropylmethyl piperidin-4-yloxy)pyridin-3-yl]-1-(morpholin-4-yl) prop-2-ene-1-one L(+)-Tartarate salt;
3-[6-(1-Isobutyl piperidin-4-yloxy)pyridin-3-yl]-1-(morpholin-4-yl) prop-2-ene-1-one L(+)-Tartarate salt;
3-[2-Chloro-4-(1-cyclobutyl piperidin-4-yloxy)phenyl]-1-(morpholin-4-yl) prop-2-ene-1-one;
3-[2-Chloro-4-(1-isopropyl piperidin-4-yloxy)phenyl]-1-(morpholin-4-yl) prop-2-ene-1-one;
3-[2-Chloro-4-(1-cyclopropylmethyl piperidin-4-yloxy)phenyl]-1-(morpholin-4-yl) prop-2-ene-1-one;
3-[2-Chloro-4-(1-isobutyl piperidin-4-yloxy)phenyl]-1-(morpholin-4-yl) prop-2-ene-1-one;
3-[4-(1-Cyclobutyl piperidin-4-yloxy)phenyl]-1-(morpholin-4-yl) prop-2-ene-1-one;
3-[4-(1-Cyclobutyl piperidin-4-yloxy)phenyl]-1-(1,1-dioxo thiomorpholin-4-yl) prop-2-ene-1-one;
3-[2-(1-Cyclobutyl piperidin-4-yloxy)pyridin-5-yl]-1-(morpholin-4-yl) prop-2-ene-1-one;
3-[2-Fluoro-4-(1-isopropyl piperidin-4-yloxy)phenyl]-1-(morpholin-4-yl) prop-2-ene-1-one;
3-[2-Fluoro-4-(1-cyclobutyl piperidin-4-yloxy)phenyl]-1-(morpholin-4-yl) prop-2-ene-1-one;
3-[4-(1-Cyclobutyl piperidin-4-yloxy)-2-methyl phenyl]-1-(morpholin-4-yl) prop-2-ene-1-one;
3-[4-(1-Isopropyl piperidin-4-yloxy)-2-methyl phenyl]-1-(morpholin-4-yl) prop-2-ene-1-one;
3-[4-(1-Cyclobutyl piperidin-4-yloxy)-3-methoxy phenyl]-1-(morpholin-4-yl) prop-2-ene-1-one;
3-[4-(1-Cyclopropylmethyl piperidin-4-yloxy)-3-methoxy phenyl]-1-(morpholin-4-yl) prop-2-ene-1-one;
3-[4-(1-Isobutyl piperidin-4-yloxy)-3-methoxy phenyl]-1-(morpholin-4-yl) prop-2-ene-1-one;
3-[4-(1-Isopropyl piperidin-4-yloxy)-3-methoxy phenyl]-1-(morpholin-4-yl) prop-2-ene-1-one;
3-[6-(1-Cyclopropylmethyl piperidin-4-yloxy)pyridin-3-yl]-1-(morpholin-4-yl) prop-2-ene-1-one; and 3-[6-(1-Isobutyl piperidin-4-yloxy)pyridin-3-yl]-1-(morpholin-4-yl) prop-2-ene-1-one;
or their pharmaceutically acceptable salts.

3. The process for preparation of a compound of formula (I) as claimed in claim 1, which comprises:
(a) reductive amination of the compound of formula (1) with compound of formula (2)

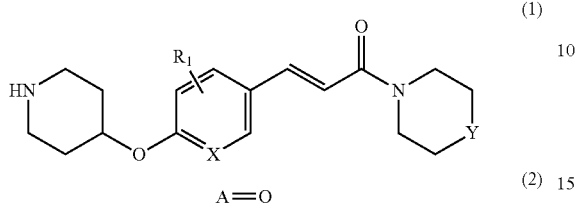

in presence of a suitable solvent and reducing agent to form a compound of formula (I), wherein all substitutions are as defined in claim 1, (b) optionally converting the compound of formula (I) to their pharmaceutically acceptable salts.

4. A pharmaceutical composition comprising a compound according to claim 1 and pharmaceutically acceptable excipients.

5. A method of treating cognitive deficits in schizophrenia, narcolepsy, obesity, attention deficit hyperactivity disorder, pain or alzheimer's disease, comprising administering to a patient in need thereof an effective amount of a compound or pharmaceutically acceptable salt thereof according to claim 1.

6. A method of treating diseases related to Histamine $H_3$ receptors selected from the group consisting of schizophrenia, narcolepsy, obesity, attention deficit hyperactivity disorder, pain or alzheimer's disease, comprising administering to a patient in need thereof an effective amount of a compound or pharmaceutically acceptable salt thereof according to claim 1.

* * * * *